(12) United States Patent
Schwarz et al.

(10) Patent No.: US 7,439,207 B2
(45) Date of Patent: Oct. 21, 2008

(54) 2,6 SUBSTITUTED PYRIDINE-3-CARBONYL DERIVATIVES SERVING AS PLANT PROTECTION AGENTS HAVING HERBICIDAL ACTION

(75) Inventors: Hans-Georg Schwarz, Langenfeld (DE); Dorothee Hoischen, Düsseldorf (DE); Kristian Kather, Langenfeld (DE); Klaus-Helmut Müller, Düsseldorf (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 527 days.

(21) Appl. No.: 10/488,456

(22) PCT Filed: Apr. 16, 2003

(86) PCT No.: PCT/EP03/03948

§ 371 (c)(1),
(2), (4) Date: Sep. 3, 2004

(87) PCT Pub. No.: WO03/092380

PCT Pub. Date: Nov. 13, 2003

(65) Prior Publication Data

US 2005/0020451 A1    Jan. 27, 2005

(30) Foreign Application Priority Data

Aug. 29, 2002   (DE) ................. 102 19 036

(51) Int. Cl.
*A01N 43/40* (2006.01)
*C07D 213/46* (2006.01)
*C07D 213/84* (2006.01)

(52) U.S. Cl. .............. 504/258; 546/286; 546/315

(58) Field of Classification Search ............ 504/258; 546/286, 315
See application file for complete search history.

(56) References Cited

U.S. PATENT DOCUMENTS

| 5,228,898 A | 7/1993 | Ueda et al. ............ 504/348 |
| 5,504,056 A | 4/1996 | Adachi et al. .......... 504/248 |
| 5,565,413 A | 10/1996 | Kanne ................. 504/254 |
| 5,834,404 A | 11/1998 | Sagae et al. ........... 504/348 |

FOREIGN PATENT DOCUMENTS

| EP | 0 791 572 | 8/1997 |
| WO | 00/15615 | 3/2000 |
| WO | 00/39094 | 7/2000 |
| WO | 01/54501 | 8/2001 |
| WO | 01/66522 | 9/2001 |
| WO | 01/94339 | 12/2001 |

OTHER PUBLICATIONS

Chem. Abstracts 116:230216 & JP 04029973, Jan. 31, 1992.
Chem. Abstracts 115:226166 & JP 03052862, Mar. 7, 1991.
Chem. Abstracts 115:29323 & JP 03038586, Feb. 19, 1991.

*Primary Examiner*—Kamal A Saeed
(74) *Attorney, Agent, or Firm*—Richard E. L. Henderson

(57) ABSTRACT

The invention relates to novel substituted pyridyl ketones of the formula

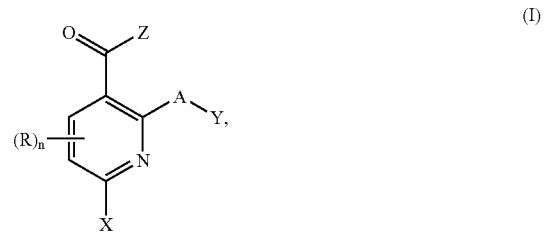

in which
A, R, X, Y, Z and n are as defined in the disclosure, to processes for preparing these novel substances, and to their use as crop treatment agents, in particular as herbicides. The invention further relates to novel intermediates of the formulae

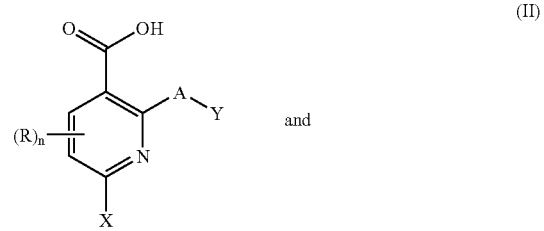

and

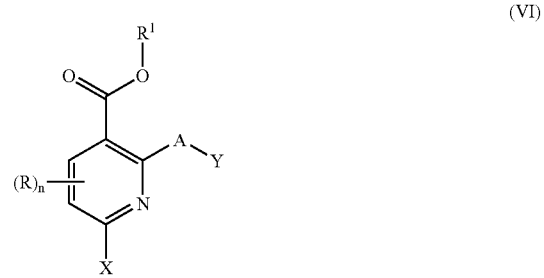

and to processes for their preparation.

3 Claims, No Drawings

2,6 SUBSTITUTED PYRIDINE-3-CARBONYL DERIVATIVES SERVING AS PLANT PROTECTION AGENTS HAVING HERBICIDAL ACTION

The present patent application has been filed under 35 U.S.C. 371 as a national stage application of PCT/EP03/03948, filed Apr. 16, 2003, which was published in German as International Patent Publication WO 03/092380 on Nov. 13, 2003, which is entitled to the right of priority of German Patent Application 102 19 036.4, filed Apr. 29, 2002.

The invention relates to novel substituted pyridyl ketones, to processes for their preparation and to their use as crop treatment agents, in particular as herbicides.

It is already known that certain substituted pyridyl ketones have herbicidal properties (cf. WO-A-01/66522, WO-A-00/39094, WO-A-00/15615, WO-A-96/17829, WO-A-96/14285/EP-A-791572, WO-A-93/01171/EP-A-641780, JP-A-04029973—cited in Chem. Abstracts 116:230216, JP-A-03052862—cited in Chem. Abstracts 115:226166, WO-A-91/00260/EP-A-432275, JP-A-03038586—cited in Chem. Abstracts 115:29323). However, the action of these compounds is not entirely satisfactory.

This invention now provides the novel substituted pyridyl ketones of the formula (I)

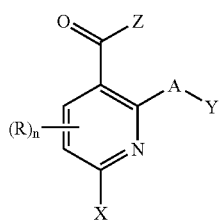

in which n represents the numbers 0, 1 or 2,

A represents alkanediyl which is optionally interrupted by O (oxygen), S (sulphur), SO or $SO_2$, or represents α- or ω-oxaalkanediyl, α,ω-dioxaalkanediyl, or α- or ω-thiaalkanediyl or α,ω-dithiaalkanediyl having in each case 1 to 6 carbon atoms, R represents nitro, cyano, carboxyl, carbamoyl, thiocarbamoyl, halogen, or represents in each case optionally cyano-, hydroxyl-, halogen- or $C_1$-$C_4$-alkoxy-substituted alkyl, alkoxy, alkylthio, alkylsulphinyl, alkylsulphonyl, alkylamino, dialkylamino or dialkylaminosulphonyl, having in each case 1 to 6 carbon atoms in the alkyl groups, X represents nitro, cyano, carboxyl, carbamoyl, thiocarbamoyl, halogen, or represents in each case optionally cyano-, hydroxyl-, halogen- or $C_1$-$C_4$-alkoxy-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups, Y represents a 4- to 12-membered, saturated or unsaturated, monocyclic or bicyclic heterocycle which contains 1 to 4 nitrogen atoms and optionally additionally an oxygen atom, a sulphur atom, an SO grouping or an $SO_2$ grouping, 1 to 3 oxo groups (C=O), 1 to 3 thioxo groups (C=S) or 1 to 3 cyanimino groups (C=N—CN) as components of the heterocycle, which is attached via a nitrogen atom to A, and which is optionally substituted by hydroxyl, mercapto, cyano, halogen, by in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkylcarbonyl, alkoxy, alkoxycarbonyl, alkylthio, alkylsulphinyl or alkylsulphonyl having in each case 1 to 6 carbon atoms in the alkyl groups, by in each case optionally halogen-substituted alkylamino or dialkylamino having in each case 1 to 6 carbon atoms in the alkyl groups, by in each case optionally halogen-substituted alkenyl, alkynyl, alkenyloxy, alkenylthio or alkenylamino having in each case 1 to 6 carbon atoms in the alkenyl or alkynyl groups, by in each case optionally halogen- and/or $C_1$-$C_4$-alkyl-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and, if appropriate, 1 to 4 carbon atoms in the alkyl moiety, or by in each case optionally halogen-, $C_1$-$C_4$-alkyl- or $C_1$-$C_4$-alkoxy-substituted phenyl, phenyloxy, phenylthio, phenylamino, benzyl, benzyloxy, benzylthio or benzylamino;

Z represents one of the groupings below

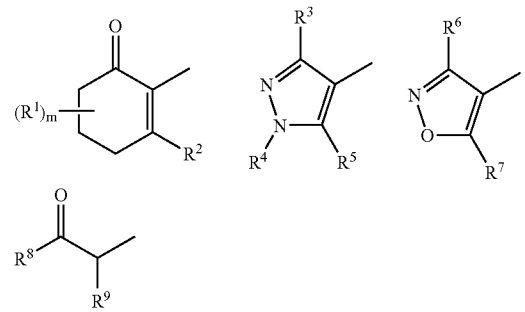

where m represents the numbers 0 to 6, $R^1$ represents halogen, represents in each case optionally cyano-, hydroxyl-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl or alkylthio having in each case 1 to 6 carbon atoms, or represents phenyl, or—if m represents 2 to 6—optionally also together with a second radical $R^1$ represents oxygen or alkanediyl (alkylene) having 2 to 5 carbon atoms, $R^2$ represents hydroxyl, formyloxy, halogen, represents in each case optionally cyano-, hydroxyl-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkoxy, alkylthio, alkylsulphinyl, alkylsulphonyl, alkylcarbonyloxy, alkoxycarbonyloxy, alkylaminocarbonyloxy, alkylsulphonyloxy or alkylsulphonylamino having in each case 1 to 6 carbon atoms, represents in each case optionally halogen-substituted alkenyloxy or alkynyloxy having in each case 3 to 6 carbon atoms, represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted aryloxy, arylthio, arylsulphinyl, arylsulphonyl, arylcarbonyloxy, arylcarbonylalkoxy, arylsulphonyloxy, arylsulphonylamino, arylalkoxy, arylalkylthio, arylalkylsulphinyl or arylalkylsulphonyl having in each case 6 or 10 carbon atoms in the aryl group and, if appropriate, 1 to 4 carbon atoms in the alkyl -moiety, or represents a grouping Y'—where Y' has the meaning given above for Y but is not in each individual case identical to Y, $R^3$ represents hydrogen, cyano, carbamoyl, thiocarbamoyl, halogen, represents in each case optionally cyano-, hydroxyl-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl or alkoxycarbonyl having in each case 1 to 6 carbon atoms in the alkyl groups, or represents optionally cyano-, halogen- or $C_1$-$C_4$-alkyl-substituted cycloalkyl having 3 to 6 carbon atoms, $R^4$ represents hydrogen, represents optionally cyano-, hydroxyl-, halogen-, $C_1$-$C_4$-alkoxy-, $C_1$-$C_4$-alkylthio- or $C_1$-$C_4$-alkylsulphinyl-substituted alkyl having 1 to 6 carbon atoms, represents in each case optionally cyano- or halogen-substituted alkenyl or alkynyl having in each case 3 to 6 carbon atoms, represents in each case optionally cyano-, halogen- or $C_1$-$C_4$-alkyl-substituted cycloalkyl or cycloalkylalkyl having in each case 3 to 6 carbon atoms in the cycloalkyl group and, if appropriate, 1 to 4 carbon atoms in the alkyl moiety, or represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted aryl or arylalkyl having in each case 6 or 10 carbon atoms in the aryl group and, if appropriate, 1 to 4 carbon atoms in the alkyl moiety, $R^5$ represents hydroxyl, formyloxy, represents in each case optionally cyano-, halogen-, $C_1$-$C_4$-alkoxy- or $C_1$-$C_4$-alkoxycarbonyl-substituted alkoxy, alkylcarbonyloxy, alkoxycarbonyloxy, alkylaminocarbonyloxy or alkylsulphonyloxy having in each case 1 to 6 carbon atoms in the alkyl groups, represents in each case optionally cyano- or halogen-substituted alkenyloxy or alkynyloxy having in each case 3 to 6 carbon atoms, or represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted arylalkoxy, arylcarbonyloxy, arylcarbonylalkoxy or arylsulphonyloxy having in each case 6 or 10 carbon atoms in the aryl group and, if appropriate, 1 to 4 carbon atoms in the alkyl moiety, $R^6$ represents hydrogen, cyano, carbamoyl, thiocarbamoyl, halogen, or represents in each case optionally cyano-, halogen- or $C_1$-$C_4$-alkoxy-substituted alkyl, alkylcarbonyl, alkoxy, alkoxycarbonyl, alkylthio, alkylsulphinyl or alkylsulphonyl having in each case 1 to 6 carbon atoms, $R^7$ represents hydrogen, represents optionally cyano-, halogen- or $C_1$-$C_4$-alkoxy-substituted alkyl having 1 to 6 carbon atoms, or represents optionally cyano-, halogen- or $C_1$-$C_4$-alkyl-substituted cycloalkyl having 3 to 6 carbon atoms, $R^8$ represents hydrogen, represents optionally cyano-, halogen- or $C_1$-$C_4$-alkoxy-substituted alkyl having 1 to 6 carbon atoms, or represents optionally cyano-, halogen- or $C_1$-$C_4$-alkyl-substituted cycloalkyl having 3 to 6 carbon atoms, and $R^9$ represents hydrogen, cyano, carbamoyl, halogen, or represents in each case optionally cyano-, halogen- or $C_1$-$C_4$-alkoxy-substituted alkyl, alkoxy, alkoxycarbonyl, alkylthio, alkylsulphinyl or alkylsulphonyl having in each case 1 to 6 carbon atoms in the alkyl groups, —including all possible tautomeric forms of the compounds of the general formula (I) and the possible salts or acid or base adducts of the compounds of the general formula (I)—.

Unless indicated otherwise, in the definitions above and below the following definitions apply:

Saturated or unsaturated hydrocarbon chains, such as alkyl, alkanediyl, alkenyl or alkynyl, are in each case straight-chain or branched, including in combination with heteroatoms, such as, for example, in alkoxy, alkylthio or alkylamino. Unless indicated otherwise, preference is given to hydrocarbon chains having 1 to 6 carbon atoms.

Cycloalkyl represents saturated, carbocyclic compounds which may optionally form a polycyclic ring system together with further carbocyclic, fused-on or bridged rings. Unless indicated otherwise, preference is given to cyclopropyl, cyclopentyl and cyclohexyl.

Aryl represents aromatic, mono- or polycyclic hydrocarbon rings, such as, for example, phenyl, naphthyl, anthranyl, phenanthryl, preferably phenyl or naphthyl, in particular phenyl.

Heterocyclyl represents saturated, unsaturated or aromatic cyclic compounds in which at least one ring member is a heteroatom, i.e. an atom different from carbon. If the ring contains a plurality of heteroatoms, these can be identical or different. Preferred heteroatoms are oxygen, nitrogen or sulphur. If this ring contains a plurality of oxygen atoms, these are not adjacent. The cyclic compounds may optionally form a polycyclic ring system together with further carbocyclic or heterocyclic fused-on or bridged rings. A polycyclic ring system may be attached via the heterocyclic ring or via a fused-on carbocyclic ring. Preference is given to mono- or bicyclic ring systems, in particular to monocyclic ring systems having 5 or 6 ring members and to bicyclic ring systems having 7 to 9 ring members.

The compounds of the general formula (I) according to the invention may, if appropriate, contain one or more symmetrically substituted carbon atoms, and they may therefore be present in different enantiomeric (R- and S-configured) or diastereomeric forms. The invention relates both to the different possible individual enantiomeric or stereoisomeric forms of the compounds of the general formula (I) and to the mixtures of these stereoisomeric compounds.

Preferred substituents or preferred ranges of the radicals present in the formulae given above and below are defined below.

n preferably represents the numbers 0 or 1.

A preferably represents alkanediyl which is optionally interrupted by O, SO or $SO_2$, or represents α- or ω-oxaalkanediyl, α,ω-dioxaalkanediyl, α- or ω-thiaalkanediyl or α,ω-dithiaalkanediyl having in each case 1 to 4 carbon atoms.

R preferably represents nitro, cyano, carboxyl, carbamoyl, thiocarbamoyl, halogen, or represents in each case optionally cyano-, hydroxyl-, halogen- or $C_1$-$C_4$-alkoxy-substituted alkyl, alkoxy, alkylthio, alkylsulphinyl, alkylsulphonyl, alkylamino, dialkylamino or dialkylaminosulphonyl having in each case 1 to 4 carbon atoms in the alkyl groups.

X preferably represents nitro, cyano, carboxyl, carbamoyl, thiocarbamoyl, halogen, or represents in each case optionally cyano-, hydroxyl-, halogen- or $C_1$-$C_4$-alkoxy-substituted alkyl, alkoxy, alkylthio, alkylsulphinyl, alkylsulphonyl, alkylamino, dialkylamino or dialkylaminosulphonyl having in each case 1 to 4 carbon atoms in the alkyl groups.

Y preferably represents a 4- to 12-membered, saturated or unsaturated, monocyclic or bicyclic heterocycle which contains 1 to 4 nitrogen atoms and optionally additionally an oxygen atom, a sulphur atom, an SO grouping, an $SO_2$ grouping, 1 or 2 oxo groups (C=O), thioxo groups (C=S) or cyanimino groups (C=N—CN) as components of the heterocycle and which is attached via a nitrogen atom to A, and which is optionally substituted by hydroxyl, mercapto, cyano, halogen, by in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkylcarbonyl, alkoxy, alkoxycarbonyl, alkylthio, alkylsulphinyl or alkylsulphonyl having in each case up to 5 carbon atoms in the alkyl groups, by in each case optionally halogen-substituted alkylamino or dialkylamino having in each case up to 5 carbon atoms in the alkyl groups, by in each case optionally halogen-substituted alkenyl, alkynyl, alkenyloxy, alkenylthio or alkenylamino having in each case up to 5 carbon atoms in the alkenyl or alkynyl groups, by in each case optionally halogen- and/or $C_1$-$C_4$-alkyl-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and, if appropriate, 1 to 4 carbon atoms in the alkyl moiety, or by in each case optionally halogen-, $C_1$-$C_4$-alkyl- or $C_1$-$C_4$-alkoxy-substituted phenyl, phenyloxy, phenylthio, phenylamino, benzyl, benzyloxy, benzylthio or benzylamino.

Z preferably represents one of the groupings below

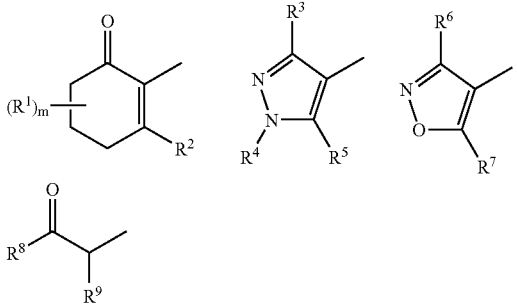

where
m represents the numbers 0 to 5, $R^1$ represents halogen, represents in each case optionally cyano-, hydroxyl-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl or alkylthio having in each case 1 to 5 carbon atoms, or represents phenyl, or—if m represents 2 to 5—optionally also together with a second radical $R^1$ represents oxygen or alkanediyl (alkylene) having 2 to 4 carbon atoms, $R^2$ represents hydroxyl, formyloxy, halogen, represents in each case optionally cyano-, hydroxyl-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkoxy, alkylthio, alkylsulphinyl, alkylsulphonyl, alkylcarbonyloxy, alkoxycarbonyloxy, alkylaminocarbonyloxy, alkylsulphonyloxy or alkylsulphonylamino having in each case 1 to 5 carbon atoms, represents in each case optionally halogen-substituted alkenyloxy or alkynyloxy having in each case 3 to 6 carbon atoms, represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted aryloxy, arylthio, arylsulphinyl, arylsulphonyl, arylcarbonyloxy, arylcarbonylalkoxy, arylsulphonyloxy, arylsulphonylamino, arylalkoxy, arylalkylthio, arylalkylsulphinyl or arylalkylsulphonyl having in each case 6 or 10 carbon atoms in the aryl group and, if appropriate, 1 to 3 carbon atoms in the alkyl moiety, or represents a grouping Y'—where Y' has the meaning given above as preferred for Y, but is not in each individual case identical to Y, $R^3$ represents hydrogen, cyano, carbamoyl, thiocarbamoyl, halogen, represents in each case optionally cyano-, hydroxyl-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl or alkoxycarbonyl having in each case 1 to 5 carbon atoms in the alkyl groups, or represents optionally cyano-, halogen- or $C_1$-$C_4$-alkyl-substituted cycloalkyl having 3 to 6 carbon atoms, $R^4$ represents hydrogen, represents optionally cyano-, hydroxyl-, halogen-, $C_1$-$C_4$-alkoxy-, $C_1$-$C_4$-alkylthio-, $C_1$-$C_4$-alkylsulphinyl-substituted alkyl having 1 to 5 carbon atoms, represents in each case optionally cyano- or halogen-substituted alkenyl or alkynyl having in each case 3 to 5 carbon atoms, represents in each case optionally cyano-, halogen- or $C_1$-$C_4$-alkyl-substituted cycloalkyl or cycloalkylalkyl having in each case 3 to 6 carbon atoms in the cycloalkyl group and, if appropriate, 1 to 4 carbon atoms in the alkyl moiety, or represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted aryl or arylalkyl having in each case 6 or 10 carbon atoms in the aryl group and, if appropriate, 1 to 3 carbon atoms in the alkyl moiety, $R^5$ represents hydroxyl, formyloxy, represents in each case optionally cyano-, halogen-, $C_1$-$C_4$-alkoxy- or $C_1$-$C_4$-alkoxy-carbonyl-substituted alkoxy, alkylcarbonyloxy, alkoxycarbonyloxy, alkylaminocarbonyloxy or alkylsulphonyloxy having in each case 1 to 5 carbon atoms in the alkyl groups, represents in each case optionally cyano- or halogen-substituted alkenyloxy or alkynyloxy having in each case 3 to 5 carbon atoms, or represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted arylalkoxy, arylcarbonyloxy, arylcarbonylalkoxy or arylsulphonyloxy having in each case 6 or 10 carbon atoms in the aryl group and, if appropriate, 1 to 3 carbon atoms in the alkyl moiety, $R^6$ represents hydrogen, cyano, carbamoyl, thiocarbamoyl, halogen, or represents in each case optionally cyano-, halogen- or $C_1$-$C_4$-alkoxy-substituted alkyl, alkylcarbonyl; alkoxy, alkoxycarbonyl, alkylthio, alkylsulphinyl or alkylsulphonyl having in each case 1 to 5 carbon atoms, $R^7$ represents hydrogen, represents optionally cyano-, halogen- or $C_1$-$C_4$-alkoxy-substituted alkyl having 1 to 5 carbon atoms, or represents optionally cyano-, halogen- or $C_1$-$C_4$-alkyl-substituted cycloalkyl having 3 to 6 carbon atoms, $R^8$ represents hydrogen, represents optionally cyano-, halogen- or $C_1$-$C_4$-alkoxy-substituted alkyl having 1 to 5 carbon atoms, or represents optionally cyano-, halogen- or $C_1$-$C_4$-alkyl-substituted cycloalkyl having 3 to 6 carbon atoms, and $R^9$ represents hydrogen, cyano, carbamoyl, halogen, or represents in each case optionally cyano-, halogen- or $C_1$-$C_4$-alkoxy-substituted alkyl, alkoxy, alkoxycarbonyl, alkylthio, alkylsulphinyl or alkylsulphonyl having in each case 1 to 5 carbon atoms in the alkyl groups.

n particularly preferably represents the number 0.

A particularly preferably represents alkanediyl which is optionally interrupted by O, S, SO or $SO_2$, or represents α- or ω-oxaalkanediyl or α- or ω-thiaalkanediyl having in each case 1, 2 or 3 carbon atoms.

R particularly preferably represents nitro, cyano, halogen, or represents in each case optionally cyano-, halogen- or $C_1$-$C_3$-alkoxy-substituted alkyl, alkoxy, alkylthio, alkylsulphinyl, alkylsulphonyl, alkylamino, dialkylamino or dialkylaminosulphonyl, having in each case 1 to 3 carbon atoms in the alkyl groups.

X particularly preferably represents nitro, cyano, halogen, or represents in each case optionally cyano-, halogen- or $C_1$-$C_3$-alkoxy-substituted alkyl, alkoxy, alkylthio, alkylsulphinyl, alkylsulphonyl, alkylamino, dialkylamino or dialkylaminosulphonyl having in each case 1 to 3 carbon atoms in the alkyl groups.

Y particularly preferably represents a 4- to 12-membered, saturated or unsaturated, monocyclic or bicyclic heterocycle which is attached to A via N (a nitrogen atom), which contains 1 to 4 nitrogen atoms and optionally additionally one oxygen atom, one sulphur atom, one SO grouping, one $SO_2$ grouping, 1 or 2 oxo groups (C=O), 1 or 2 thioxo groups (C=S) or one cyanimino group (C=N—CN) as components of the heterocycle and which is optionally substituted by cyano, halogen, by in each case optionally cyano-, halogen-, $C_1$-$C_3$-alkoxy-, $C_1$-$C_3$-alkylthio-, $C_1$-$C_3$-alkylsulphinyl- or $C_1$-$C_3$-alkylsulphonyl-substituted alkyl, alkylcarbonyl, alkoxy, alkoxycarbonyl, alkylthio, alkylsulphinyl or alkylsulphonyl having in each case up to 4 carbon atoms in the alkyl groups, by in each case optionally halogen-substituted alkylamino or dialkylamino having in each case up to 4 carbon atoms in the alkyl groups, by in each case optionally halogen-substituted alkenyl, alkynyl, alkenyloxy, alkenylthio or alkenylamino having in each case up to 4 carbon atoms in the alkenyl or alkynyl groups, by in each case optionally halogen- and/or $C_1$-$C_3$-alkyl-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and, if appropriate, 1 to 3 carbon atoms in the alkyl moiety, or by in each case optionally halogen-, $C_1$-$C_4$-alkyl- or $C_1$-$C_4$-alkoxy-substituted phenyl, phenyloxy, phenylthio, phenylamino, benzyl, benzyloxy, benzylthio or benzylamino.

Z particularly preferably represents one of the groupings below

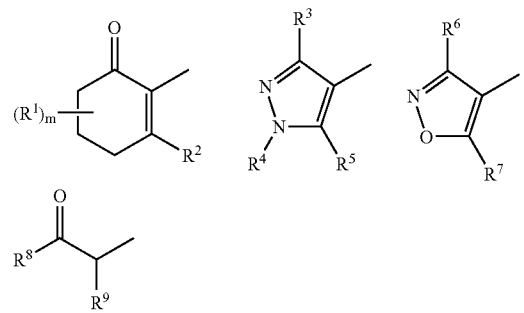

where m represents the numbers 0 to 4, $R^1$ represents halogen, represents in each case optionally cyano-, hydroxyl-, halogen-, $C_1$-$C_3$-alkoxy-, $C_1$-$C_3$-alkylthio-, $C_1$-$C_3$-alkylsulphinyl- or $C_1$-$C_3$-alkylsulphonyl-substituted alkyl or alkylthio having in each case 1 to 4 carbon atoms, or represents phenyl, or—if m represents 2 to 5—optionally also together with a second radical $R^1$ represents oxygen or alkanediyl (alkylene) having 2 or 3 carbon atoms, $R^2$ represents hydroxyl, formyloxy, halogen, represents in each case optionally cyano-, hydroxyl-, halogen-, $C_1$-$C_3$-alkoxy-, $C_1$-$C_3$-alkylthio-, $C_1$-$C_3$-alkylsulphinyl- or $C_1$-$C_3$-alkylsulphonyl-substituted alkoxy, alkylthio, alkylsulphinyl, alkylsulphonyl, alkylcarbonyloxy, alkoxycarbonyloxy, alkylaminocarbonyloxy, alkylsulphonyloxy or alkylsulphonylamino having in each case 1 to 4 carbon atoms, represents in each case optionally halogen-substituted alkenyloxy or alkynyloxy having in each case 3 to 5 carbon atoms, represents in each case optionally nitro-, cyano-, halogen-, $C_1$-$C_3$-alkyl-, $C_1$-$C_3$-haloalkyl-, $C_1$-$C_3$-alkoxy-, $C_1$-$C_3$-haloalkoxy-, $C_1$-$C_3$-alkylthio-, $C_1$-$C_3$-haloalkylthio-, $C_1$-$C_3$-alkylsulphinyl-, $C_1$-$C_3$-haloalkylsulphinyl-, $C_1$-$C_3$-alkylsulphonyl- or $C_1$-$C_3$-haloalkylsulphonyl-substituted aryloxy, arylthio, arylsulphinyl, arylsulphonyl, arylcarbonyloxy, arylcarbonylalkoxy, arylsulphonyloxy, arylsulphonylamino, arylalkoxy, arylalkylthio, arylalkylsulphinyl or arylalkylsulphonyl having in each case 6 or 10 carbon atoms in the aryl group and, if appropriate, 1 or 2 carbon atoms in the alkyl moiety, or represents a grouping Y'—where Y' has the meaning given above as being particularly preferred for Y, but is not in each individual case identical to Y, $R^3$ represents hydrogen, cyano, carbamoyl, thiocarbamoyl, halogen, represents in each case optionally cyano-, hydroxyl-, halogen-, $C_1$-$C_3$-alkoxy-, $C_1$-$C_3$-alkylthio-, $C_1$-$C_3$-alkylsulphinyl- or $C_1$-$C_3$-alkylsulphonyl-substituted alkyl, alkoxy, alkylthio, alkylsulphinyl, alkylsulphonyl or alkoxycarbonyl having in each case 1 to 4 carbon atoms in the alkyl groups, or represents optionally cyano-, halogen- or $C_1$-$C_3$-alkyl-substituted cycloalkyl having 3 to 6 carbon atoms, $R^4$ represents hydrogen, represents optionally cyano-, hydroxyl-, halogen-, $C_1$-$C_3$-alkoxy-, $C_1$-$C_3$-alkylthio-, $C_1$-$C_3$-alkylsulphinyl- or $C_1$-$C_3$-alkylsulphonyl-substituted having 1 to 4 carbon atoms, represents in each case optionally cyano- or halogen-substituted alkenyl or alkynyl having in each case 3 or 4 carbon atoms, represents in each case optionally cyano-, halogen- or $C_1$-$C_3$-alkyl-substituted cycloalkyl or cycloalkylalkyl having in each case 3 to 6 carbon atoms in the cycloalkyl group and, if appropriate, 1 to 3 carbon atoms in the alkyl moiety, or represents in each case optionally nitro-, cyano-, halogen-, $C_1$-$C_3$-alkyl-, $C_1$-$C_3$-haloalkyl-, $C_1$-$C_3$-alkoxy-, $C_1$-$C_3$-haloalkoxy-, $C_1$-$C_3$-alkylthio-, $C_1$-$C_3$-haloalkylthio-, $C_1$-$C_3$-alkylsulphinyl-, $C_1$-$C_3$-haloalkylsulphinyl-, $C_1$-$C_3$-alkylsulphonyl- or $C_1$-$C_3$-haloalkylsulphonyl-substituted aryl or arylalkyl having in each case 6 or 10 carbon atoms in the aryl group and, if appropriate, 1 or 2 carbon atoms in the alkyl moiety, $R^5$ represents hydroxyl, formyloxy, represents in each case optionally cyano-, halogen-, $C_1$-$C_3$-alkoxy- or $C_1$-$C_3$-alkoxy-carbonyl-substituted alkoxy, alkylcarbonyloxy, alkoxycarbonyloxy, alkylaminocarbonyloxy or alkylsulphonyloxy having in each case 1 to 4 carbon atoms in the alkyl groups, represents in each case optionally cyano- or halogen-substituted alkenyloxy or alkynyloxy having in each case 3 or 4 carbon atoms, or represents in each case optionally nitro-, cyano-, halogen-, $C_1$-$C_3$-alkyl-, $C_1$-$C_3$-haloalkyl-, $C_1$-$C_3$-alkoxy-, $C_1$-$C_3$-haloalkoxy-, $C_1$-$C_3$-alkylthio-, $C_1$-$C_3$-haloalkylthio-, $C_1$-$C_3$-alkylsulphinyl-, $C_1$-$C_3$-haloalkylsulphinyl-, $C_1$-$C_3$-alkylsulphonyl- or $C_1$-$C_3$-haloalkylsulphonyl-substituted arylalkoxy, arylcarbonyloxy, arylcarbonylalkoxy or arylsulphonyloxy having in each case 6 or 10 carbon atoms in the aryl group and, if appropriate, 1 or 2 carbon atoms in the alkyl moiety, $R^6$ represents hydrogen, cyano, carbamoyl, thiocarbamoyl, halogen, or represents in each case optionally cyano-, halogen- or $C_1$-$C_3$-alkoxy-substituted alkyl, alkylcarbonyl, alkoxy, alkoxycarbonyl, alkylthio, alkylsulphinyl or alkylsulphonyl having in each case 1 to 4 carbon atoms, $R^7$ represents hydrogen, represents optionally cyano-, halogen- or $C_1$-$C_3$-alkoxy-substituted alkyl having 1 to 4 carbon atoms, or represents optionally cyano-, halogen- or $C_1$-$C_3$-alkyl-substituted cycloalkyl having 3 to 6 carbon atoms, $R^8$ represents hydrogen, represents optionally cyano-, halogen- or $C_1$-$C_3$-alkoxy-substituted alkyl having 1 to 4 carbon atoms, or represents optionally cyano-, halogen- or $C_1$-$C_3$-alkyl-substituted cycloalkyl having 3 to 6 carbon atoms, and $R^9$ represents hydrogen, cyano, carbamoyl, halogen, or represents in each case optionally cyano-, halogen- or $C_1$-$C_3$-alkoxy-substituted alkyl, alkoxy, alkoxycarbonyl, alkylthio, alkylsulphinyl or alkylsulphonyl having in each case 1 to 4 carbon atoms in the alkyl groups.

A very particularly preferably represents methylene, ethane-1,2-diyl (dimethylene), 1-oxaethane-1,2-diyl, 2-oxaethane-1,2-diyl, 1-thiaethane-1,2-diyl, 2-thiaethane-1,2-diyl, propane-1,2-diyl, propane-1,3-diyl (trimethylene), 1-oxapropane-1,3-diyl, 2-oxapropane-1,3-diyl, 3-oxapropane-1,3-diyl, 1-thiapropane-1,3-diyl or 3-thiapropane-1,3-diyl.

R very particularly preferably represents nitro, cyano, fluorine, chlorine, bromine, represents in each case optionally cyano-, fluorine-, chlorine-, methoxy- or ethoxy-substituted methyl, ethyl, methoxy or ethoxy, represents in each case optionally fluorine- and/or chlorine-substituted methylthio, ethylthio, methylsulphinyl, ethylsulphinyl, methylsulphonyl or ethylsulphonyl, or represents methylamino, ethylamino, dimethylamino or dimethylaminosulphonyl.

X very particularly preferably represents nitro, cyano, fluorine, chlorine, bromine, represents in each case optionally cyano-, fluorine-, chlorine-, methoxy- or ethoxy-substituted methyl, ethyl, methoxy or ethoxy, represents in each case optionally fluorine- and/or chlorine-substituted methylthio, ethylthio, methylsulphinyl, ethylsulphinyl, methylsulphonyl or ethylsulphonyl, or represents methylamino, ethylamino, dimethylamino or dimethylaminosulphonyl.

Y very particularly preferably represents a heterocycle, attached to A via nitrogen, from the group consisting of pyrrolidinyl, oxopyrrolidinyl, pyrrolyl, indolyl, pyrazolyl, imidazolyl, imidazolinyl, imidazolidinyl, oxoimidazolinyl, 2-oxo-1,3-diazacyclopentyl, 2-oxo-1,3-diazacyclopentenyl, oxazolidinyl, 2-oxo-1,3-oxazacyclopentyl (2-oxooxazolidinyl), 1,2-oxazacyclopentyl (isoxazolidinyl), 1,2-oxazacyclohexyl, thiazolidinyl, cyaniminothiazolidinyl, oxotriazolinyl, thioxotriazolinyl, oxotetrazolinyl, piperidinyl, oxopiperidinyl, 2-oxo-1,3-diazacyclohexyl, 2-oxo-1-azacycloheptyl, 2-oxo-1,3-diazacycloheptyl, morpholinyl, piperazinyl, which heterocycle is optionally substituted by cyano, fluorine, chlorine, bromine, by in each case optionally cyano-, fluorine-, chlorine-, bromine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl, by in each case optionally fluorine- and/or chlorine-substituted methylamino; ethylamino, n- or i-propylamino, dimethylamino or diethylamino, by in each case optionally fluorine-, chlorine- and/or bromine-substituted ethenyl, propenyl, butenyl, ethynyl, propynyl, butynyl, propenyloxy, butenyloxy, propenylthio, butenylthio, propenylamino or butenylamino, by in each case optionally fluorine-, chlorine-, methyl- or ethyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or by in each case optionally fluorine-, chlorine-, bromine-, methyl-, ethyl-, n- or i-propyl-, n-, i-, s- or t-butyl-, methoxy-, ethoxy-, n- or i-propoxy-substituted phenyl, phenyloxy, phenylthio, phenylamino, benzyl, benzyloxy, benzylthio or benzylamino.

Z very particularly preferably represents one of the groupings below

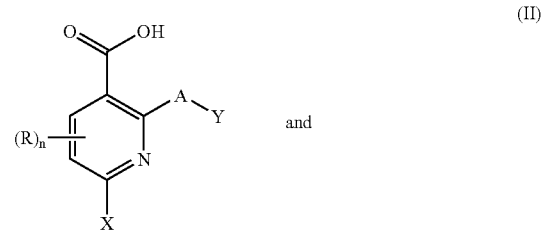

(II)

and

-continued

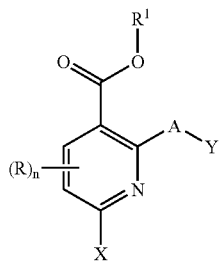

(VI)

where m represents the numbers 0 to 3, $R^1$ represents fluorine, chlorine, bromine, or represents in each case optionally cyano-, fluorine-, chlorine-, bromine-, methoxy-, ethoxy, methylthio-, ethylthio-, methylsulphinyl-, ethylsulphinyl-, methylsulphonyl- or ethylsulphonyl-substituted methyl, ethyl, n- or i-propyl, methylthio, ethylthio, n- or i-propylthio, or represents phenyl, or—if m represents 2 or 3—optionally also together with a second radical $R^1$ represents oxygen, methylene or dimethylene (ethane-1,2-diyl).

$R^2$ represents hydroxyl, chlorine, represents in each case optionally fluorine-, chlorine-, methoxy-, ethoxy-, methylthio-, ethylthio-, methylsulphinyl-, ethylsulphinyl-, methylsulphonyl- or ethylsulphonyl-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, methylsulphonyloxy, ethylsulphonyloxy, methylsulphonylamino or ethylsulphonylamino, represents is each case optionally fluorine-, chlorine- and/or bromine-substituted propenyloxy, butenyloxy, propynyloxy, butynyloxy, represents in each case optionally nitro-, cyano-, fluorine-, chlorine-, bromine-, methyl-, ethyl-, n- or i-propyl-, difluoromethyl-, trifluoromethyl-, chlorodifluoromethyl-, methoxy-, ethoxy-, n- or i-propoxy-, difluoromethoxy-, trifluoromethoxy-, methylthio-, ethylthio-, n- or i-propylthio-, difluoromethylthio, trifluoromethylthio-, methylsulphinyl-, ethylsulphinyl-, trifluoromethylsulphinyl-, methylsulphonyl-, ethylsulphonyl-, trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylsulphonylamino, phenylmethoxy, phenylmethylthio, phenylmethylsulphinyl or phenylmethylsulphonyl, $R^3$ represents hydrogen, cyano, fluorine, chlorine, bromine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, or represents in each case optionally cyano-, fluorine-, chlorine-, bromine-, methyl-, n- or i-propyl-substituted cyclopropyl, cyclobutyl, cyclopentyl or cyclohexyl, $R^4$ represents hydrogen, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally cyano-, fluorine-, chlorine- and/or bromine-substituted propenyl, butenyl, propynyl or butynyl, represents in each case optionally cyano-, fluorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methylthio-, ethylthio-, n- or i-propylthio-, trifluoromethylthio-, methylsulphinyl-, ethylsulphinyl-, trifluoromethylsulphinyl, methylsulphonyl-, ethylsulphonyl- or- trifluoromethylsulphonyl-substituted phenyl or phenylmethyl, $R^5$ represents hydroxyl, formyloxy, represents in each case optionally cyano-, fluorine-, chlorine-, methoxy-, ethoxy-, n- or i-propoxy-, methoxycarbonyl-, ethoxycarbonyl-, n- or i-propoxycarbonyl-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally cyano-, fluorine-, chlorine- or bromine-substituted propenyloxy, butenyloxy, propynyloxy or butynyloxy, or represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methylthio-, ethylthio-, n- or i-propylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenylmethoxy, phenylcarbonyloxy, phenylcarbonylmethoxy or phenylsulphonyloxy, $R^6$ represents hydrogen, cyano, fluorine, chlorine, bromine, or represents in each case optionally cyano-, fluorine-, chlorine-, methoxy-, ethoxy-, n- or i-propoxy-substituted methyl, ethyl, n- or i-propyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl, $R^7$ represents hydrogen, represents in each case optionally cyano-, fluorine-, chlorine-, bromine-, methoxy-, ethoxy-, n- or i-propoxy-substituted methyl, ethyl, n- or i-propyl, or represents in each case optionally cyano-, fluorine-, chlorine-, bromine-, methyl-, ethyl-, n- or i-propyl-substituted cyclopropyl, cyclobutyl, cyclopentyl or cyclohexyl, $R^8$ represents hydrogen, represents in each case optionally cyano-, fluorine-, chlorine-, methoxy-, ethoxy-, n- or i-propoxy-substituted methyl, ethyl, n- or i-propyl, or represents in each case optionally cyano-, fluorine-, chlorine-, methyl-, ethyl-, n- or i-propyl-substituted cyclopropyl, cyclobutyl, cyclopentyl or cyclohexyl, and $R^9$ represents hydrogen, cyano, fluorine, chlorine, bromine, or represents in each case optionally cyano-, fluorine-, chlorine-, methoxy-, ethoxy-, n- or i-propoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl.

Particular emphasis is given to compounds of the formula (I)

in which n, A, X and Y are as defined above and

Z represents one of the groupings below

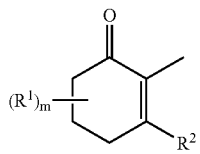 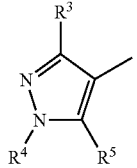

where m represents the numbers 0 to 3, $R^1$ represents fluorine, chlorine, bromine, represents in each case optionally cyano-, fluorine-, chlorine-, bromine-, methoxy-, ethoxy-, methylthio-, ethylthio-, methylsulphinyl-, ethylsulphinyl-, methylsulphonyl- or ethylsulphonyl-substituted methyl, ethyl, methylthio, ethylthio, or represents phenyl, $R^2$ represents hydroxyl, represents in each case optionally fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methoxy, ethoxy, n- or i-propoxy, methylthio, ethylthio, n- or i-propylthio, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, methylsulphonyloxy, ethylsulphonyloxy, methylsulphonylamino or ethylsulphonylamino, represents in each case optionally fluorine- and/or chlorine-substituted propenyloxy, butenyloxy, propynyloxy, butynyloxy, represents in each case optionally nitro-, cyano-, fluorine-, chlorine-, bromine-, methyl-, ethyl-, n- or i-propyl-, trifluoromethyl-, methoxy-, ethoxy-, difluoromethoxy-, trifluoromethoxy-, methylthio-, ethylthio-, trifluoromethylthio-, methylsulphinyl-, ethylsulphinyl-, trifluoromethylsulphinyl-, methylsulphonyl-, ethylsulphonyl-, trifluoromethylsulphonyl-substituted phenyloxy, phenylthio, phenylcarbonyloxy, phenylcarbonylmethoxy, phenylsulphonyloxy, phenylsulphonylamino, penylmethoxy, phenylmethylthio, $R^3$ represents hydrogen, represents in each case optionally fluorine-, chlorine-, methoxy-, ethoxy-, methylthio-, ethylthio-, methylsulphinyl-, ethylsulphinyl-, methylsulphonyl- or ethylsulphonyl-substituted methyl or ethyl, represents methoxy, ethoxy, methylthio, ethylthio, methylsulphinyl, ethylsulphinyl, methylsulphonyl, ethylsulphonyl, methoxycarbonyl, ethoxycarbonyl, n- or i-propoxycarbonyl, or represents cyclopropyl, $R^4$ represents methyl, ethyl, n- or i-propyl, $R^5$ represents hydroxyl, represents in each case optionally fluorine-, chlorine-, methoxy-, ethoxy-, n- or i-propoxy-, methoxycarbonyl-, ethoxycarbonyl-, n- or i-propoxycarbonyl-substituted methoxy, ethoxy, n- or i-propoxy, represents acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine-, chlorine- or bromine-substituted propenyloxy, butenyloxy, propynyloxy or butynyloxy, or represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methylthio-, ethylthio-, n- or i-propylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenylmethoxy, phenylcarbonyloxy, phenylcarbonylmethoxy or phenylsulphonyloxy.

Particular emphasis is furthermore given to compounds of the formula (I) in which n, R, A, X and Z are as defined above and Y represents a substituted 4- to 12-membered saturated or unsaturated, monocyclic or bicyclic heterocycle which contains 1 to 3 nitrogen atoms, one oxo group and, if appropriate, additionally one oxygen atom, one sulphur atom, one SO grouping or one $SO_2$ grouping, 1 or 2 oxo groups (C=O), 1 or 2 thioxo groups (C=S) or 1 to 3 cyanimino groups (C=N—CN) as components of the heterocycle, which is attached to A via a nitrogen atom and which is optionally substituted by hydroxyl, mercapto, cyano, halogen, by in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkylcarbonyl, alkoxy, alkoxycarbonyl, alkylthio, alkylsulphinyl or alkylsulphonyl having in each case 1 to 6 carbon atoms in the alkyl groups, by in each case optionally halogen-substituted alkylamino or dialkylamino having in each case 1 to 6 carbon atoms in the alkyl groups, by in each case optionally halogen-substituted alkenyl, alkynyl, alkenyloxy, alkenylthio or alkenylamino having in each case 1 to 6 carbon atoms in the alkenyl or alkynyl groups, by in each case optionally halogen- and/or $C_1$-$C_4$-alkyl-substituted cycloalkyl, cyaloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl groups and, if appropriate, 1 to 4 carbon atoms in the alkyl moiety, or by in each case optionally halogen-, $C_1$-$C_4$-alkyl- or $C_1$-$C_4$-alkoxy-substituted phenyl, phenyloxy, phenylthio, phenylamino, benzyl, benzyloxy, benzylthio or benzylamino.

Particular emphasis is furthermore given to compounds of the formula (I) in which n represents the number 0, A represents methylene, X represents chlorine, cyano, methoxy, methylsulphonyl or trifluoromethyl, Y represents in each case optionally methyl-, ethyl-, n- or i-propyl-, n-, i-, s- or t-butyl-substituted 2-oxo-1,3-diazacyclopentyl or 2-oxo-1,3-diazacyclohexyl or represents in each case optionally methyl-, ethyl-, methoxy-, ethoxy-, methylthio- or ethylthio-substituted oxotriazolinyl or oxotetrazolinyl, and Z represents one of the groupings below

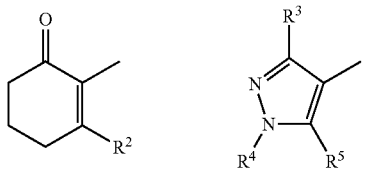

where

R² represents hydroxyl, represents in each case optionally fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methoxy, ethoxy, n- or i-propoxy, methylthio, ethylthio, n- or i-propylthio, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, methylsulphonyloxy, ethylsulphonyloxy, methylsulphonylamino or ethylsulphonylamino, represents in each case optionally fluorine- and/or chlorine-substituted propenyloxy, butenyloxy, propynyloxy, butynyloxy, represents in each case optionally nitro-, cyano-, fluorine-, chlorine-, bromine-, methyl-, ethyl-, n- or i-propyl-, trifluoromethyl-, methoxy-, ethoxy-, difluoromethoxy-, trifluoromethoxy-, methylthio-, ethylthio-, trifluoromethylthio-, methylsulphinyl-, ethylsulphinyl-, trifluoromethylsulphinyl-, methylsulphonyl-, ethylsulphonyl-, trifluoromethylsulphonyl-substituted phenyloxy, phenylthio, phenylcarbonyloxy, phenylcarbonylmethoxy, phenylsulphonyloxy, phenylsulphonylamino, penylmethoxy, phenylmethylthio, R³ represents hydrogen, represents in each case optionally fluorine-, chlorine-, methoxy-, ethoxy-, methylthio-, ethylthio-, methylsulphinyl-, ethylsulphinyl-, methylsulphonyl- or ethylsulphonyl-substituted methyl or ethyl, represents methoxy, ethoxy, methylthio, ethylthio, methylsulphinyl, ethylsulphinyl, methylsulphonyl, ethylsulphonyl, methoxycarbonyl, ethoxycarbonyl, n- or i-propoxycarbonyl, or represents cyclopropyl, R⁴ represents methyl, ethyl, n- or i-propyl, R⁵ represents hydroxyl, represents in each case optionally fluorine-, chlorine-, methoxy-, ethoxy-, n- or i-propoxy-, methoxycarbonyl-, ethoxycarbonyl-, n- or i-propoxycarbonyl-substituted methoxy, ethoxy, n- or i-propoxy, represents acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine-, chlorine- or bromine-substituted propenyloxy, butenyloxy, propynyloxy or butynyloxy, or represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methylthio-, ethylthio-, n- or i-propylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenylmethoxy, phenylcarbonyloxy, phenylcarbonylmethoxy or phenylsulphonyloxy.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

The abovementioned general or preferred radical definitions apply both to the end products of the formula (I) and, correspondingly, to the starting materials or intermediates required in each case for the preparation. These radical definitions can be combined with one another as desired, i.e. including combinations between the given preferred ranges. Moreover, individual definitions may not apply.

The novel substituted pyridyl ketones of the formula (I) have strong and selective herbicidal activity.

The novel substituted pyridyl ketones of the formula (I) are obtained when substituted pyridinecarboxylic acids of the general formula (II)

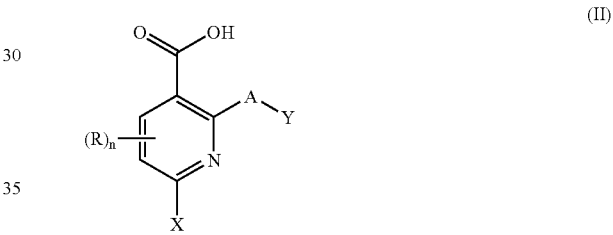

in which n, A, R, X and Y are as defined above,

—or reactive derivatives thereof, such as, for example, the corresponding acid halides, acid cyanides or esters— are reacted with compounds of the general formula (III)

in which

Z is as defined above, if appropriate in the presence of a dehydrating agent and if appropriate in the presence of one or more reaction auxiliaries and if appropriate in the presence of one or more diluents, and, if appropriate, the resulting compounds of the general formula (I) are, after the process according to the invention has been carried out, subjected to subsequent reactions (for example substitution, oxidation or reduction reactions) for conversion into other compounds of the general formula (I) within the scope of the definition of the substituents, by customary methods.

Using, for example, 6-chloro-2-(3-methyl-2-oxoimidazolidin-1-ylmethyl)nicotinic acid and cyclohexane-1,3-dione as starting materials, the course of the reaction during the process according to the invention can be illustrated by the formula scheme below:

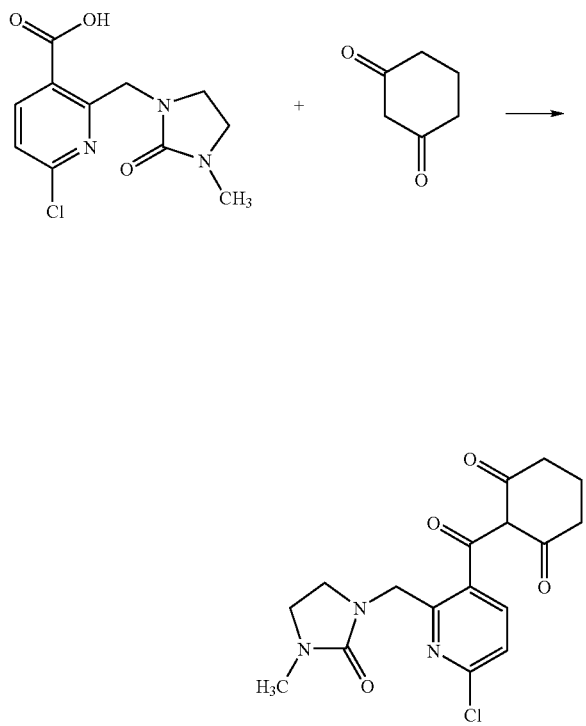

The formula (II) provides a general definition of the substituted pyridinecarboxylic acids to be used as starting materials in the process according to the invention for preparing compounds of the general formula (I). In the general formula (II), n, A, R, X and Y preferably have those meanings which have already been mentioned above, in connection with the description of the compounds of the general formula (I) according to the invention, as being preferred, particularly preferred, very particularly preferred or most preferred for n, A, R, X and Y. The starting materials of the general formula (II) have hitherto not been disclosed in the literature and, as novel substances, they also form part of the subject-matter of the present application.

The formula (III) provides a general definition of the compounds further to be used as starting materials in the process according to the invention for preparing compounds of the general formula (I). In the general formula (III), Z preferably has that meaning which has already been given above, in connection with the description of the compounds of the general formula (I) according to the invention, as being preferred, particularly preferred, very particularly preferred or most preferred for Z. The starting materials of the general formula (III) are known organic chemicals for synthesis.

The process according to the invention for preparing compounds of the formula (I) is preferably carried out in the presence of one or more reaction auxiliaries. Suitable reaction auxiliaries are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore, also basic organic nitrogen compounds, such as, for example, trimethylamine, triethylamine, tripropylamine, tributylamine, ethyl-diisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl, 2,6-dimethyl-, 3,4-dimethyl- and 3,5-dimethylpyridine, 5-ethyl-2-methylpyridine, 4-dimethylaminopyridine, N-methylpiperidine, N-ethylpiperidine, N-methylmorpholine, N-ethylmorpholine, 1,4-diazabicyclo [2.2.2]octane (DABCO), 1,5-diazabicyclo[4.3.0]non-5-ene (DBN) or 1,8-diazabicyclo[5.4.0]undec-7-ene (DBU).

The process according to the invention for preparing compounds of the formula (I) is, if appropriate, carried out using a dehydrating agent. Suitable dehydrating agents are the customary chemicals suitable for binding water. Examples which may be mentioned are dicyclohexylcarbodiimide, carbonyl-bisimidazole and propanephosphonic anhydride, preferably dicyclohexylcarbodiimide and propanephosphonic anhydride.

The process according to the invention for preparing the compounds of the general formula (I) is preferably carried out using one or more diluents. Suitable diluents are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone, or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide.

When carrying out the process according to the invention for preparing compounds of the formula (I), the reaction temperatures can be varied within a relatively wide range. In general, the process is carried out at temperatures between 0° C. and 150° C., preferably between 10° C. and 120° C.

The process according to the invention for preparing compounds of the formula (I) is generally carried out under atmospheric pressure. However, it is also possible to carry out the process according to the invention under elevated or reduced pressure—in general between 0.1 bar and 10 bar.

For carrying out the process according to the invention for preparing compounds of the formula (I), the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours. Work-up is carried out by customary methods (cf. the Preparation Examples).

The novel substituted pyridinecarboxylic acids of the general formula (II) are obtained when substituted pyridinecarboxylic acid esters of the general formula (IV)

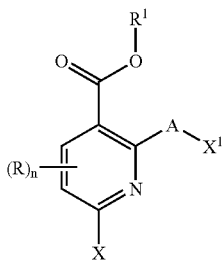

(IV)

in which n, A, R and X are as defined above,

R¹ represents alkyl (in particular methyl, ethyl, n- or i-propyl, n-, i-, s- or t-butyl) or represents arylalkyl (in particular benzyl) and X¹ represents halogen (in particular chlorine or bromine), are, in a first step, reacted with compounds of the general formula (V)

M—Y  (V)

in which

Y is as defined above and

M represents hydrogen or a metal equivalent (in particular lithium, sodium or potassium), if appropriate in the presence of one or more reaction auxiliaries and if appropriate in the presence of one or more diluents, and the resulting carboxylic acid esters of the general formula (VI)

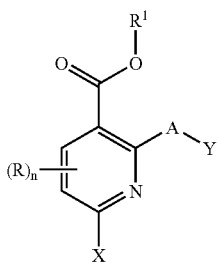

(VI)

are, in a second step, converted by customary methods into the carboxylic acids of the formula (II).

The formula (IV) provides a general definition of the substituted pyridinecarboxylic acid esters to be used as starting materials in the process according to the invention for preparing compounds of the general formula (II). In the general formula (IV), n, A, R, X preferably have those meanings which have already been mentioned above, in connection with the description of the compounds of the general formula (I) according to the invention, as being preferred, particularly preferred, very particularly preferred or most preferred for n, A, R, X.

The formula (V) provides a general definition of the compounds further to be used as starting materials in the process according to the invention for preparing compounds of the general formula (II). In the general formula (V), Y preferably has that meaning which has already been mentioned above, in connection with the description of the compounds of the general formula (I) according to the invention, as being preferred, particularly preferred, very particularly preferred or most preferred for Y. The starting materials of the general formula (V) are known organic chemicals for synthesis.

The process according to the invention for preparing compounds of the formula (II) is preferably carried out in the presence of one or more reaction auxiliaries. Suitable reaction auxiliaries are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or L-propoxide, n-, i-, s- or t-butoxide or potassium methoxide, ethoxide, n- or i-propoxide, n-, i-, s- or t-butoxide; furthermore, also basic organic nitrogen compounds, such as, for example, trimethylamine, triethylamine, tripropylamine, tributylamine, ethyl-diisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl, 2,6-dimethyl-, 3,4-dimethyl- and 3,5-dimethylpyridine, 5-ethyl-2-methylpyridine, 4-dimethylaminopyridine, N-methylpiperidine, N-ethylpiperidine, N-methylmorpholine, N-ethylmorpholine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU). Preference is given to sodium hydride, potassium carbonate and triethylamine.

The process according to the invention for preparing the compounds of the general formula (II) is preferably carried out using one or more diluents. Suitable diluents for the first step are especially inert organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran (THF) or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide (DMF), N,N-dimethylacetamide, N-methylformanilide, N-methylpyrrolidone or hexamethylphosphoric triamide; esters, such as methyl acetate or ethyl acetate; sulphoxides, such as dimethyl sulphoxide. Preference is given to acetonitrile, THF and DMF. Suitable diluents for the second step are especially inert organic solvents and their aqueous mixtures. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran (THF) or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide (DMF), N,N-dimethylacetamide, N-methylformanilide, N-methylpyrrolidone or hexamethylphosphoric triamide; esters, such as methyl acetate or ethyl acetate; sulphoxides, such as dimethyl sulphoxide. Preference is given to THF and to mixtures of THF and water.

When carrying out the process according to the invention for preparing the compounds of the general formula (II), the reaction temperatures can be varied within a relatively wide range. In general, the process is carried out at temperatures between 0° C. and 150° C., preferably between 10° C. and 120° C., with particular preference between 20° C. and the boiling point of the diluent used.

The process according to the invention for preparing the compounds of the general formula (II) is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours.

Work-up is carried out by customary methods, for example by filtration, recrystallization or chromatography (cf. the Preparation Examples).

The compounds of the formula (VI) can either be converted directly ("in situ") into the compounds of the formula (II) or be isolated prior to further reactions.

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine; Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds can be converted into the customary formulations, such as solutions, emulsions, wettable powders, suspensions, powders, dusts, pastes, soluble powders, granules, suspoemulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example, ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in their formulations, can also be used as mixtures with known herbicides and/or with substances which improve the compatibility with crop plants ("safeners"), finished formulations or tank mixes being possible. Also possible therefore are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flufenpyr, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, ketospiradox, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargon acid, pendimethalin, pendralin, penoxysulam, pentoxazone, pethoxamid, phenmedipham, picolinafen, piperophos, pretilachlor, primisulfuron (-methyl), profluazol, profoxydim, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example

AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention- can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention—also in combination with other agro-chemical active compounds—, better plant growth, increased tolerance of the crop plants to high or low temperatures, increased tolerance of the crop plants to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The preferred transgenic plants or plant cultivars (i.e. those obtained by genetic engineering) which are to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized in particular are increased defence of the plants against insects by toxins formed in the plants, in particular those formed in the plants by the genetic material from *Bacillus thuringiensis* (for example by the genes CryIA(a), CryIA (b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in each case can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula I or the active compound mixtures according to the invention, where in addition to the good control of weed plants, the abovementioned synergistic effects with the transgenic plants or plant cultivars occur. The preferred ranges stated above for the active compounds or mixtures also apply to the treatment of these plants. Particular emphasis is given to the treatment of plants with the compounds or mixtures specifically mentioned in the present text.

The following examples illustrate the preparation and use of the active compounds according to the invention.

PREPARATION EXAMPLES

Example 1

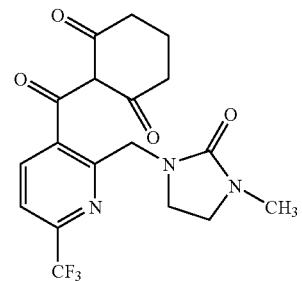

A mixture of 1.00 g (3.63 mmol) of 6-trifluoromethyl-2-(3-methyl-2-oxoimidazolidin-1-ylmethyl)nicotinic acid, 0.41 g (3.63 mmol) of cyclohexane-1,3-dione, 0.90 g (4.35 mmol) of dicyclohexylcarbodiimide and 30 ml of acetonitrile is stirred at room temperature (about 20° C.) for 18 hours. 0.75 g (7.25 mmol) of triethylamine and 0.15 g (1.45 mmol) of trimethylsilyl cyanide are then added to this mixture, and the reaction mixture is stirred at room temperature for 18 hours. The mixture is then concentrated under reduced pressure and the residue is stirred with 10% strength aqueous sodium carbonate solution, diethyl ether is added and the mixture is filtered. The aqueous phase of the filtrate is separated off, acidified with 2N hydrochloric acid and extracted with methylene chloride. The solution of the organic extract is washed with water, dried with sodium sulphate and filtered. The filtrate is concentrated and the residue is purified by preparative HPLC (High Performance Liquid Chromatography).

This gives 0.23 g (16% of theory) of 2-[2-(3-methyl-2-oxoimidazolidin-1-ylmethyl)-6-trifluoromethylpyridine-3-carbonyl]cyclohexane-1,3-dione.

logP=2.14.

Analogously to Example 1, and in accordance with the general description of the preparation process according to the invention, it is also possible to prepare, for example, the compounds of the general formula (I) listed in Table 1 below.

TABLE 1

Examples of the compounds of the formula (I)
Here, n represents in each case the number 0

| Ex. No. | A | X | Y | Z | Phys. data |
|---|---|---|---|---|---|
| 2 | $CH_2$ | $CF_3$ | (1-methyl-4-methyl-5-oxo-3-(methylthio)-1,2,4-triazole) | 2-methylcyclohexane-1,3-dione | logP = 2.23 [a] |
| 3 | $CH_2$ | $CF_3$ | (1-methyl-4-methyl-5-oxo-3-(methylthio)-1,2,4-triazole) | 1-ethyl-4-methyl-5-hydroxypyrazole | logP = 1.79 [a] |
| 4 | $CH_2$ | $CF_3$ | (1-methyl-4-methyl-5-oxo-3-(methylthio)-1,2,4-triazole) | 1,4-dimethyl-5-hydroxypyrazole | logP = 1.49 [a] |
| 5 | $CH_2$ | $CF_3$ | (1-methyl-4-methyl-5-oxo-3-(methoxy)-1,2,4-triazole) | 2-methylcyclohexane-1,3-dione | logP = 2.01 [a] |
| 6 | $CH_2$ | $CF_3$ | (1-methyl-4-methyl-5-oxo-3-(methoxy)-1,2,4-triazole) | 1-ethyl-4-methyl-5-hydroxypyrazole | logP = 1.59 [a] |

TABLE 1-continued

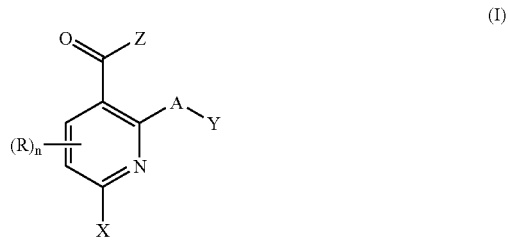

Examples of the compounds of the formula (I)
Here, n represents in each case the number 0

| Ex. No. | A | X | Y | Z | Phys. data |
|---|---|---|---|---|---|
| 7 | $CH_2$ | $CF_3$ | (1,4-dimethyl-5-oxo-triazol-3-yl)-O-CH3 | 1-methyl-4-methyl-5-OH pyrazole | logP = 1.36 [a] |
| 8 | $CH_2$ | $SO_2CH_3$ | 1,3-dimethyl-2-oxo-imidazolidinyl | 2-methyl-1,3-cyclohexanedione | |
| 9 | $CH_2$ | $SO_2CH_3$ | 1,3-dimethyl-2-oxo-imidazolidinyl | 1-ethyl-4-methyl-5-OH pyrazole | |
| 10 | $CH_2$ | $SO_2CH_3$ | 1,3-dimethyl-2-oxo-tetrahydropyrimidinyl | 2-methyl-1,3-cyclohexanedione | |
| 11 | $CH_2$ | $SO_2CH_3$ | 1,3-dimethyl-2-oxo-tetrahydropyrimidinyl | 1-ethyl-4-methyl-5-OH pyrazole | |
| 12 | $CH_2$ | $CF_3$ | 1,4-dimethyl-5-oxo-tetrazolyl | 2-methyl-1,3-cyclohexanedione | |
| 13 | $CH_2$ | $CF_3$ | 1,4-dimethyl-5-oxo-tetrazolyl | 1-ethyl-4-methyl-5-OH pyrazole | |

TABLE 1-continued

Examples of the compounds of the formula (I)
Here, n represents in each case the number 0

| Ex. No. | A | X | Y | Z | Phys. data |
|---|---|---|---|---|---|
| 14 | $CH_2$ | $SO_2CH_3$ | 1,4-dimethyl-tetrazol-5(4H)-one | 2-methylcyclohexane-1,3-dione | |
| 15 | $CH_2$ | $SO_2CH_3$ | 1,4-dimethyl-tetrazol-5(4H)-one | 1-ethyl-5-hydroxy-4-methyl-pyrazole | |
| 16 | $CH_2$ | $OCH_3$ | 1,3-dimethyl-imidazolidin-2-one | 2-methylcyclohexane-1,3-dione | |
| 17 | $CH_2$ | $OCH_3$ | 1,3-dimethyl-imidazolidin-2-one | 1-ethyl-5-hydroxy-4-methyl-pyrazole | |
| 18 | $CH_2$ | Cl | 1,3-dimethyl-tetrahydropyrimidin-2-one | 2-methylcyclohexane-1,3-dione | |
| 19 | $CH_2$ | Cl | 1,3-dimethyl-tetrahydropyrimidin-2-one | 1-ethyl-5-hydroxy-4-methyl-pyrazole | |
| 20 | $CH_2$ | $CF_3$ | 1,3-dimethyl-imidazolidin-2-one | 2-methyl-3-(phenylthio)cyclohex-2-enone | |

TABLE 1-continued

Examples of the compounds of the formula (I)
Here, n represents in each case the number 0

| Ex. No. | A | X | Y | Z | Phys. data |
|---|---|---|---|---|---|
| 21 | CH₂ | CF₃ | (1,3-dimethyl-2-oxoimidazolidin-1-yl) | 2-methyl-3-(methylsulfonylamino)cyclohex-2-en-1-one | |
| 22 | OCH₂ | CF₃ | (5-methyl-2-oxopyrrolidin-1-yl) | 2-methylcyclohexane-1,3-dione | logP = 2.09 a) |
| 23 | OCH₂ | CF₃ | (5-methyl-2-oxopyrrolidin-1-yl) | 1-ethyl-5-hydroxy-4-methyl-1H-pyrazol-3-yl | logP = 1.66 a) |
| 24 | CH₂ | CF₃ | (1,3-dimethyl-2-oxoimidazolidin-1-yl) | 1-ethyl-5-hydroxy-4-methyl-1H-pyrazol-3-yl | logP = 1.54 a) |
| 25 | CH₂ | CF₃ | (2-methyl-1,1-dioxoisothiazolidin-2-yl) | 1-ethyl-5-hydroxy-4-methyl-1H-pyrazol-3-yl | logP = 1.64 a) |
| 26 | CH₂ | CF₃ | (2-methyl-1,1-dioxoisothiazolidin-2-yl) | 2-methylcyclohexane-1,3-dione | logP = 2.19 a) |
| 27 | CH₂ | CF₃ | (3-methyl-2-oxooxazolidin-3-yl) | 1-ethyl-5-hydroxy-4-methyl-1H-pyrazol-3-yl | logP = 1.49 a) |
| 28 | CH₂ | CF₃ | (3-methyl-2-oxooxazolidin-3-yl) | 2-methylcyclohexane-1,3-dione | logP = 1.97 a) |

TABLE 1-continued

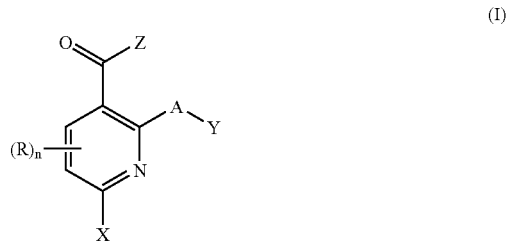

Examples of the compounds of the formula (I)
Here, n represents in each case the number 0

| Ex. No. | A | X | Y | Z | Phys. data |
|---|---|---|---|---|---|
| 29 | $CH_2$ | $CF_3$ | (1-methyl-3-ethyl-imidazolidin-2-one-yl) | (2-methyl-cyclohexane-1,3-dione-yl) | logP = 2.31 [a] |
| 30 | $CH_2$ | $CF_3$ | (1-methyl-3-ethyl-imidazolidin-2-one-yl) | (1-ethyl-4-methyl-5-hydroxy-pyrazol-yl) | logP = 1.75 [a] |
| 31 | $CH_2$ | $CF_3$ | (1-methyl-3-ethyl-imidazolidin-2-one-yl) | (1-methyl-4-methyl-5-hydroxy-pyrazol-yl) | logP = 1.51 [a] |
| 32 | $CH_2$ | $CF_3$ | (1-methyl-3-ethyl-imidazolidin-2-one-yl) | (1,3,4-trimethyl-5-hydroxy-pyrazol-yl) | logP = 1.41 [a] |
| 33 | $CH_2$ | $CF_3$ | (1,3-dimethyl-tetrahydropyrimidin-2-one-yl) | (2-methyl-cyclohexane-1,3-dione-yl) | logP = 2.19 [a] |

The logP values given in the table were determined in accordance with EEC Directive 79/831 Annex V.A8 by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—corresponding measurement results in Table 1 are marked [a].

(b) Mobile phases for the determination in the neutral range: 0.01 molar aqueous phosphate buffer solution, acetonitrile; linear gradient from 10% acetonitrile to 90% acetonitrile—corresponding measurement results in Table 1 are marked [b].

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

Starting materials of the formula (II):

Example II-1:

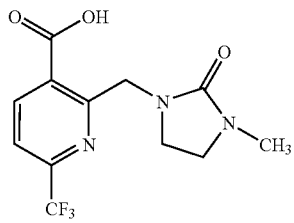

Step 1

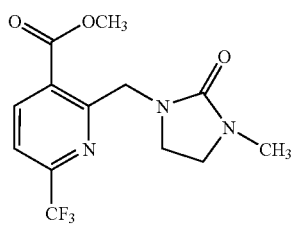

A mixture of 6.2 g (62.0 mmol) of 1-methyl-2-oxoimidazolidine, 2.5 g (62.0 mmol) of sodium hydride and 100 ml of acetonitrile is stirred at 80° C. for 60 minutes. At room temperature (about 20° C.), 18.5 g (62.0 mmol) of methyl 2-bromomethyl-6-trifluoromethyl nicotinate are then added, and the reaction mixture is stirred at room temperature for 18 hours. 100 ml of water are then added carefully, and the mixture is then acidified with 2N hydrochloric acid and shaken with methylene chloride. The organic phase is separated off, washed with water, dried with sodium sulphate and filtered. The filtrate is concentrated under reduced pressure and the residue is purified by column chromatography (silica gel, methylene chloride/acetonitrile, 9:1 v/v).

3.2 g (13% of theory) of methyl 6-trifluoromethyl-2-(3-methyl-2-oxoimidazolidin-1-ylmethyl)nicotinate are obtained as second fraction.

logP=1.99.

Step 2

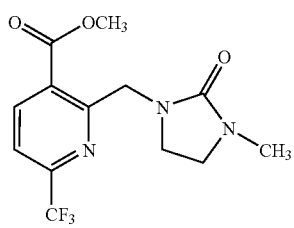

A mixture of 2.8 g (8.8 mmol) of methyl 6-trifluoromethyl-2-(3-methyl-2-oxoimidazolidin-1-ylmethyl)nicotinate, 0.35 g of sodium hydroxide, 50 ml of water and 50 ml of tetrahydrofuran is stirred at room temperature (about 20° C.) for 18 hours. The mixture is then concentrated under reduced pressure to about half its original volume and then diluted with water and shaken with diethyl ether. The aqueous phase is separated off, acidified with 2N hydrochloric acid and extracted with ethyl acetate. The solution of the organic extract is washed with water and then concentrated under reduced pressure. The residue is digested with diethyl ether and the resulting crystalline product is isolated by filtration with suction.

This gives 1.2 g (43% of theory) of—6-trifluoromethyl-2-(3-methyl-2-oxoimidazolidin-1-ylmethyl)nicotinic acid.

logP=1.62

Analogously, it is also possible to prepare, for example, the compounds of the formulae (II) and (VI) listed in Tables 2 and 3, respectively, below.

TABLE 2

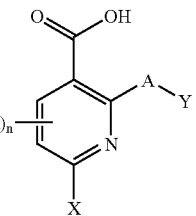

(II)

Examples of the compounds of the formula (II)
(Here, n represents in each case the number 0)

| Ex. No. | A | X | Y | Phys. data |
|---|---|---|---|---|
| II-2 | CH$_2$ | CF$_3$ | ![triazolone-OCH3] | logP = 1.52 [a)] |
| II-3 | CH$_2$ | CF$_3$ | ![triazolone-SCH3] | logP = 1.72 [a)] |
| II-4 | CH$_2$ | SO$_2$CH$_3$ | ![oxoimidazolidine] | |
| II-5 | CH$_2$ | CF$_3$ | ![oxotetrahydropyrimidine] | logP = 1.82 [a)] |
| II-6 | CH$_2$ | SO$_2$CH$_3$ | ![oxotetrahydropyrimidine] | |
| II-7 | CH$_2$ | CF$_3$ | ![triazinone] | |

TABLE 2-continued

Examples of the compounds of the formula (II)
(Here, n represents in each case the number 0)

| Ex. No. | A | X | Y | Phys. data |
|---|---|---|---|---|
| II-8 | CH₂ | SO₂CH₃ | 1,4-dimethyl-tetrazol-5(4H)-one-yl | |
| II-9 | CH₂ | OCH₃ | 1,3-dimethyl-imidazolidin-2-one-yl | |
| II-10 | CH₂ | OCH₃ | 1,3-dimethyl-tetrahydropyrimidin-2-one-yl | |
| II-11 | CH₂ | OCH₃ | 1,4-dimethyl-tetrazol-5(4H)-one-yl | |
| II-12 | CH₂ | Cl | 1,3-dimethyl-imidazolidin-2-one-yl | |
| II-13 | CH₂ | Cl | 1,3-dimethyl-tetrahydropyrimidin-2-one-yl | |
| II-14 | CH₂ | Cl | 1,4-dimethyl-tetrazol-5(4H)-one-yl | |
| II-15 | CH₂ | CN | 1,3-dimethyl-imidazolidin-2-one-yl | |
| II-16 | CH₂ | CN | 1,3-dimethyl-tetrahydropyrimidin-2-one-yl | |
| II-17 | CH₂ | CN | 1,4-dimethyl-tetrazol-5(4H)-one-yl | |
| II-18 | CH₂ | CH₃ | 1,3-dimethyl-imidazolidin-2-one-yl | |
| II-19 | CH₂ | CH₃ | 1,3-dimethyl-tetrahydropyrimidin-2-one-yl | |
| II-20 | CH₂ | CH₃ | 1,4-dimethyl-tetrazol-5(4H)-one-yl | |
| II-21 | CH₂ | CF₃ | 2-methyl-isothiazolidine 1,1-dioxide-yl | logP = 1.59 [a] |
| II-22 | CH₂ | CF₃ | 3-methyl-oxazolidin-2-one-yl | |
| II-23 | CH₂ | CF₃ | 1-methyl-3-ethyl-imidazolidin-2-one-yl | logP = 1.86 [a] |

TABLE 3

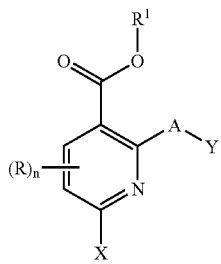

Examples of the compounds of the formula (VI)
(Here, n represents in each case the number 0)

| Ex. No. | A | R¹ | X | Y | Phys. data |
|---|---|---|---|---|---|
| VI-1 | $CH_2$ | $CH_3$ | $CF_3$ | 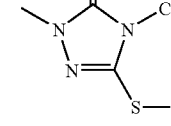 | logP = 2.14 [a] |
| VI-2 | $CH_2$ | $CH_3$ | $CF_3$ | 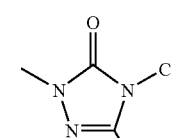 | logP = 1.88 [a] |
| VI-3 | $CH_2$ | $CH_3$ | $SO_2CH_3$ | 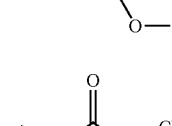 | |
| VI-4 | $CH_2$ | $CH_3$ | $CF_3$ | 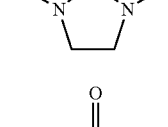 | |
| VI-5 | $CH_2$ | $CH_3$ | $SO_2CH_3$ | 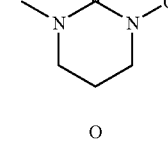 | |
| VI-6 | $CH_2$ | $CH_3$ | $CF_3$ | 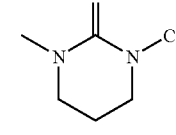 | |
| VI-7 | $CH_2$ | $CH_3$ | $SO_2CH_3$ | 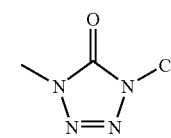 | |

TABLE 3-continued

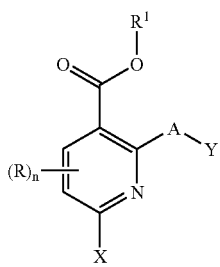

Examples of the compounds of the formula (VI)
(Here, n represents in each case the number 0)

| Ex. No. | A | R¹ | X | Y | Phys. data |
|---|---|---|---|---|---|
| VI-8 | $CH_2$ | $CH_3$ | $OCH_3$ | | |
| VI-9 | $CH_2$ | $CH_3$ | $OCH_3$ | | |
| VI-10 | $CH_2$ | $CH_3$ | $OCH_3$ | | |
| VI-11 | $CH_2$ | $CH_3$ | Cl | | |
| VI-12 | $CH_2$ | $CH_3$ | Cl | | |
| VI-13 | $CH_2$ | $CH_3$ | Cl | | |
| VI-14 | $CH_2$ | $CH_3$ | CN | | |
| VI-15 | $CH_2$ | $CH_3$ | CN | | |

TABLE 3-continued

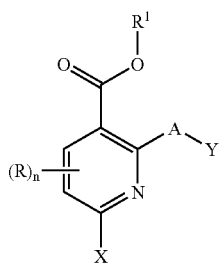

Examples of the compounds of the formula (VI)
(Here, n represents in each case the number 0)

| Ex. No. | A | R¹ | X | Y | Phys. data |
|---|---|---|---|---|---|
| VI-16 | CH₂ | CH₃ | CN | 1,4-dimethyl-tetrazol-5-one | |
| VI-17 | CH₂ | CH₃ | CH₃ | 1,3-dimethyl-imidazolidin-2-one | |
| VI-18 | CH₂ | CH₃ | CH₃ | 1,3-dimethyl-tetrahydropyrimidin-2-one | |
| VI-19 | CH₂ | CH₃ | CH₃ | 1,4-dimethyl-tetrazol-5-one | |
| VI-20 | CH₂ | CH₃ | CF₃ | 1-methyl-3-t-butyl-tetrahydropyrimidin-2-one | |
| VI-21 | CH₂ | CH₃ | CF₃ | 1,4-dimethyl-tetrazol-5-one | |
| VI-22 | CH₂ | CH₃ | CF₃ | 3-methyl-oxazolidin-2-one | logP = 1.88 a) |
| VI-23 | CH₂ | t-C₄H₉ | CF₃ | 3,4-dimethyl-5-(methylthio)-1,2,4-triazol-5(4H)-one | |

TABLE 3-continued

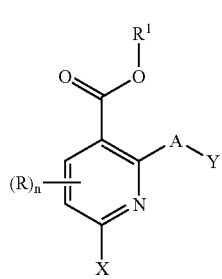

Examples of the compounds of the formula (VI)
(Here, n represents in each case the number 0)

| Ex. No. | A | R¹ | X | Y | Phys. data |
|---|---|---|---|---|---|
| VI-24 | CH₂ | t-C₄H₉ | CF₃ | 3,4-dimethyl-5-methoxy-1,2,4-triazol-5(4H)-one | |
| VI-25 | CH₂ | t-C₄H₉ | SO₂CH₃ | 1,3-dimethyl-imidazolidin-2-one | |
| VI-26 | CH₂ | t-C₄H₉ | CF₃ | 1,3-dimethyl-tetrahydropyrimidin-2-one | |
| VI-27 | CH₂ | t-C₄H₉ | SO₂CH₃ | 1,3-dimethyl-tetrahydropyrimidin-2-one | |
| VI-28 | CH₂ | t-C₄H₉ | CF₃ | 1,4-dimethyl-tetrazol-5-one | |
| VI-29 | CH₂ | t-C₄H₉ | SO₂CH₃ | 1,4-dimethyl-tetrazol-5-one | |
| VI-30 | CH₂ | t-C₄H₉ | OCH₃ | 1,3-dimethyl-imidazolidin-2-one | |

TABLE 3-continued

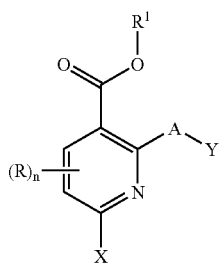

Examples of the compounds of the formula (VI)
(Here, n represents in each case the number 0)

| Ex. No. | A | R¹ | X | Y | Phys. data |
|---|---|---|---|---|---|
| VI-31 | $CH_2$ | $t\text{-}C_4H_9$ | $OCH_3$ | (1,3-dimethyl-2-oxotetrahydropyrimidin-1-yl) | |
| VI-32 | $CH_2$ | $t\text{-}C_4H_9$ | $OCH_3$ | (1,4-dimethyl-5-oxo-tetrazol-1-yl) | |
| VI-33 | $CH_2$ | $t\text{-}C_4H_9$ | Cl | (1,3-dimethyl-2-oxoimidazolidin-1-yl) | |
| VI-34 | $CH_2$ | $t\text{-}C_4H_9$ | Cl | (1,3-dimethyl-2-oxotetrahydropyrimidin-1-yl) | |
| VI-35 | $CH_2$ | $t\text{-}C_4H_9$ | Cl | (1,4-dimethyl-5-oxo-tetrazol-1-yl) | |
| VI-36 | $CH_2$ | $t\text{-}C_4H_9$ | CN | (1,3-dimethyl-2-oxoimidazolidin-1-yl) | |
| VI-37 | $CH_2$ | $t\text{-}C_4H_9$ | CN | (1,3-dimethyl-2-oxotetrahydropyrimidin-1-yl) | |
| VI-38 | $CH_2$ | $t\text{-}C_4H_9$ | CN | (1,4-dimethyl-5-oxo-tetrazol-1-yl) | |

TABLE 3-continued

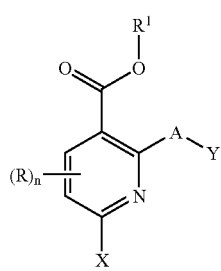

Examples of the compounds of the formula (VI)
(Here, n represents in each case the number 0)

| Ex. No. | A | R¹ | X | Y | Phys. data |
|---|---|---|---|---|---|
| VI-39 | $CH_2$ | $t\text{-}C_4H_9$ | $CH_3$ | (1,3-dimethyl-2-oxoimidazolidin-1-yl) | |
| VI-40 | $CH_2$ | $t\text{-}C_4H_9$ | $CH_3$ | (1,3-dimethyl-2-oxotetrahydropyrimidin-1-yl) | |
| VI-41 | $CH_2$ | $t\text{-}C_4H_9$ | $CH_3$ | (1,4-dimethyl-5-oxo-tetrazol-1-yl) | |
| VI-42 | $CH_2$ | $t\text{-}C_4H_9$ | $CF_3$ | (1-methyl-3-t-butyl-2-oxotetrahydropyrimidin-1-yl) | |
| VI-43 | $CH_2$ | $t\text{-}C_4H_9$ | $CF_3$ | (1,4-dimethyl-5-oxo-tetrazol-1-yl) | |
| VI-44 | $CH_2$ | $t\text{-}C_4H_9$ | $CF_3$ | (3-methyl-2-oxo-oxazolidin-3-yl) | |
| VI-45 | $CH_2$ | $CH_3$ | $CF_3$ | (1-methyl-3-ethyl-2-oxoimidazolidin-1-yl) | logP = 2.24 [a)] |
| VI-46 | $CH_2$ | $CH_3$ | $CF_3$ | (2-methyl-1,1-dioxoisothiazolidin-2-yl) | logP = 2.07 [a)] |

USE EXAMPLES

Example A

Pre-Emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is supplied per unit area. The concentration of active compound in the spray liquor is chosen such that the particular amount of active compound desired is applied in 1000 litres of water per hectare.

After three weeks, the degree of damage to the plants is rated in % damage in comparison to the development of the untreated control. The figures denote:
0%=no effect (like untreated control)
100%=total destruction In this test, for example, the compounds of Preparation Examples 1, 2, 3, 4, 5 and 6 exhibit strong activity against weeds, and some of them are tolerated well by crop plants, such as, for example, maize, soybean and wheat.

Example B

Post-Emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1 000 1 l of water/ha.

After three weeks, the degree of damage to the plants is rated in % damage in comparison to development of the untreated control.

The figures denote:
0%=no effect (like untreated control)
100%=total destruction In this test, for example, the compounds of Preparation Examples 1, 2, 3, 4 and 5 exhibit strong activity against weeds, and most of them are tolerated well by crop plants, such as, for example, maize and oilseed rape.

The invention claimed is:
1. A compound of formula (I)

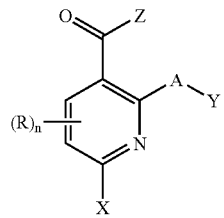

(I)

including any tautomeric forms thereof or salts or acid or base adducts of a compound of formula (I) including any tautomeric forms thereof, in which n represents the numbers 0, 1, or 2, A represents methylene, R represents nitro, cyano, carboxyl, carbamoyl, thiocarbamoyl, or halogen; or represents optionally cyano-, hydroxyl-, halogen-, or $C_1$-$C_4$-alkoxy-substituted alkyl, alkoxy, alkylthio, alkylsulphinyl, alkylsulphonyl, alkylamino, dialkylamino, or dialkylaminosulphonyl, having in each case 1 to 6 carbon atoms in the alkyl groups, X represents nitro, cyano, carboxyl, carbamoyl, thiocarbamoyl, or halogen; or represents optionally cyano-, hydroxyl-, halogen-, or $C_1$-$C_4$-alkoxy-substituted alkyl, alkoxy, alkylthio, alkylsulphinyl, alkylsulphonyl, alkylamino, dialkylamino, or dialkylaminosulphonyl having in each case 1 to 6 carbon atoms in the alkyl groups, Y represents a 4- to 12-membered, saturated or unsaturated, monocyclic or bicyclic heterocycle that contains 1 to 4 nitrogen atoms and optionally additionally an oxygen atom, a sulphur atom, an SO group, an $SO_2$ group, 1 to 3 oxo groups (C=O), 1 to 3 thioxo groups (C=S), or 1 to 3 cyanimino groups (C=N—CN) as components of the heterocycle, wherein the heterocycle is attached via a nitrogen atom to A and is optionally substituted by hydroxyl, mercapto, cyano, or halogen, by optionally cyano-, halogen-, $C_1$-$C_4$-alkoxy-, $C_1$-$C_4$-alkylthio-, $C_1$-$C_4$-alkylsulphinyl-, or $C_1$-$C_4$-alkylsulphonyl-substituted alkyl, alkylcarbonyl, alkoxy, alkoxycarbonyl, alkylthio, alkylsulphinyl, or alkylsulphonyl having in each case 1 to 6 carbon atoms in the alkyl groups, by optionally halogen-substituted alkylamino or dialkylamino having in each case 1 to 6 carbon atoms in the alkyl groups, by optionally halogen-substituted alkenyl, alkynyl, alkenyloxy, alkenylthio, or alkenylamino having in each case 1 to 6 carbon atoms in the alkenyl or alkynyl groups, by optionally halogen- and/or $C_1$-$C_4$-alkyl-substituted cycloalkyl, cycloalkyloxy, cycloalkylthio, cycloalkylamino, cycloalkylalkyl, cycloalkylalkoxy, cycloalkylalkylthio, or cycloalkylalkylamino having in each case 3 to 6 carbon atoms in the cycloalkyl groups and, where appropriate, 1 to 4 carbon atoms in any alkyl moiety, or by optionally halogen-, $C_1$-$C_4$-alkyl-, or $C_1$-$C_4$-alkoxy-substituted phenyl, phenyloxy, phenylthio, phenylamino, benzyl, benzyloxy, benzylthio, or benzylamino; and Z represents

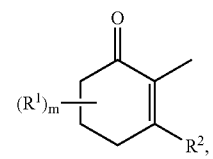

where m represents the numbers 0 to 6, $R^1$ represents halogen; represents optionally cyano-, hydroxyl-, halogen-, $C_1$-$C_4$-alkoxy-, $C_1$-$C_4$-alkylthio-, $C_1$-$C_4$-alkylsulphinyl-, or $C_1$-$C_4$-alkylsulphonyl-substituted alkyl or alkylthio having in each case 1 to 6 carbon atoms; or represents phenyl; or, when m represents 2 to 6, two radicals $R^1$ optionally together represent oxygen or alkanediyl (alkylene) having 2 to 5 carbon atoms, and $R^2$ represents hydroxyl, formyloxy, or halogen; represents optionally cyano-, hydroxyl-, halogen-, $C_1$-$C_4$-alkoxy-, $C_1$-$C_4$-alkylthio-, $C_1$-$C_4$-alkylsulphinyl-, or $C_1$-$C_4$-alkylsulphonyl-substituted alkoxy, alkylthio, alkylsulphinyl, alkylsulphonyl, alkylcarbonyloxy, alkoxycarbonyloxy, alkylaminocarbonyloxy, alkylsulphonyloxy, or alkylsulphonylamino having in each case 1 to 6 carbon atoms; represents optionally halogen-substituted alkenyloxy or alkynyloxy having in each case 3 to 6 carbon atoms; represents optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, or $C_1$-$C_4$-haloalkylsulphonyl-substituted aryloxy, arylthio, arylsulphinyl, arylsulphonyl, arylcarbonyloxy, arylcarbonylalkoxy, arylsulphonyloxy, arylsulphonylamino, arylalkoxy, arylalkylthio, arylalkylsulphinyl, or arylalkylsulphonyl having in each case 6 or 10 carbon atoms in the aryl group and, where appropriate, 1 to 4 carbon atoms in any alkyl moiety; or represents a group Y' having the meanings given for Y but not being identical to Y.

2. A compound according to claim 1 in which

Y represents a heterocycle attached to A via a nitrogen atom selected from the group consisting of pyrrolidinyl, oxopyrrolidinyl, pyrrolyl, indolyl, pyrazolyl, imidazolyl, imidazolinyl, imidazolidinyl, oxoimidazolinyl, 2-oxo-1,3-diazacyclopentyl, 2-oxo-1,3-diazacyclopentenyl, oxazolidinyl, 2-oxo-1,3-oxazacyclopentyl (2-oxooxazolidinyl), 1,2-oxazacyclopentyl (isoxazolidinyl), 1,2-oxazacyclohexyl, thiazolidinyl, cyaniminothiazolidinyl, oxotriazolinyl, thioxotriazolinyl, oxotetrazolinyl, piperidinyl, oxopiperidinyl, 2-oxo-1,3-diazacyclohexyl, 2-oxo-1-azacycloheptyl, 2-oxo-1,3-diazacycloheptyl, morpholinyl, and piperazinyl, wherein the heterocycle is optionally substituted by cyano, fluorine, chlorine, or bromine, by optionally cyano-, fluorine-, chlorine-, bromine-, methoxy-, ethoxy-, methylthio-, ethylthio-, methylsulphinyl-, ethylsulphinyl-, methylsulphonyl-, or ethylsulphonyl-substituted methyl, ethyl, n- or i-propyl, n-, i-, s-, or t-butyl, acetyl, propionyl, n- or i-butyroyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl, or ethylsulphonyl, by optionally fluorine- and/or chlorine-substituted methylamino, ethylamino, n- or i-propylamino, dimethylamino, or diethylamino, by optionally fluorine-, chlorine-, and/or bromine-substituted ethenyl, propenyl, butenyl, ethynyl, propynyl, butynyl, propenyloxy, butenyloxy, propenylthio, butenylthio, propenylamino, or butenylamino, by optionally fluorine-, chlorine-, methyl-, or ethyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino, or cyclohexylmethylamino, or by optionally fluorine-, chlorine-, bromine-, methyl-, ethyl-, n- or i-propyl-, n-, i-, s-, or t-butyl-, methoxy-, ethoxy-, or n- or i-propoxy-substituted phenyl, phenyloxy, phenylthio, phenylamino, benzyl, benzyloxy, benzylthio, or benzylamino.

3. A pesticide comprising one or more compounds of formula (I) according to claim 1.

* * * * *